(12) United States Patent
Blaustein et al.

(10) Patent No.: US 6,564,940 B2
(45) Date of Patent: *May 20, 2003

(54) ELECTRIC TOOTHBRUSH

(75) Inventors: Lawrence A. Blaustein, Moreland Hills, OH (US); John R. Nottingham, Hunting Valley, OH (US); John Osher, Moreland Hills, OH (US); John W. Spirk, Gates Mills, OH (US); Douglas A. Gall, Westlake, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/861,834

(22) Filed: May 21, 2001

(65) Prior Publication Data

US 2001/0054561 A1 Dec. 27, 2001

Related U.S. Application Data

(63) Continuation-in-part of application No. 09/710,616, filed on Nov. 9, 2000, now Pat. No. 6,371,294, which is a continuation-in-part of application No. 09/382,745, filed on Aug. 25, 1999, now Pat. No. 6,178,579, which is a continuation-in-part of application No. 09/236,794, filed on Jan. 25, 1999, now Pat. No. 6,189,693, which is a continuation-in-part of application No. 09/163,621, filed on Sep. 30, 1998, now Pat. No. 6,000,083.

(51) Int. Cl.⁷ ........................... A46B 13/02; B65D 83/00
(52) U.S. Cl. ........................ 206/362.2; 15/22.1; 15/28; 200/318.2; 206/470
(58) Field of Search ................................ 15/22.1, 22.2, 15/28, DIG. 10; 200/1 B, 43.16, 43.18, 318, 318.1, 318.2; 206/320, 362.2, 470

(56) References Cited

U.S. PATENT DOCUMENTS 1,476,433 A    12/1923   Vandervoort
1,947,324 A     2/1934   Zerbee (List continued on next page.)

FOREIGN PATENT DOCUMENTS

CA    1191003    7/1985
CN    2223981    4/1996

(List continued on next page.)

OTHER PUBLICATIONS website: http://www.crest.com/products/toothbrushes/prod_brushes_content_fl.htr (Nov. 2000).

Sgan–Cohen, Harold D.; Babayof, Itai; Zadik, Dan; Mann, Jonathan, "One Month Evaluation of the Manually Rotating 'Bio–Bright' Toothbrush for Clinical Safety and Efficacy", Department of Community Dentistry, Faculty of Dental Medicine, Hebrew University–Hadassah, Jerusalem, Israel, J Clin Dent 6: pp. 120–123, 1995.

(List continued on next page.)

*Primary Examiner*—Randall E. Chin
(74) *Attorney, Agent, or Firm*—Fay, Sharpe, Fagan, Minnich & McKee, LLP (57) ABSTRACT

An electric toothbrush includes a head having a moving portion, a handle, and shaft between the head and the handle. A body portion is hollow and further includes a motor operative to generate motion for driving the moving portion. A battery is located within the hollow section for powering the motor. A first switch, operatively connected to the motor provides momentary operation of the toothbrush. Optionally, a second switch provides for continuous operation of the toothbrush. The first switch can be operated while the toothbrush is in a toothbrush package, such as, for example, a plastic blister pack. A consumer can momentarily observe the operation of the toothbrush before purchasing the toothbrush. The consumer cannot operate the second switch and is thereby prevented from leaving the toothbrush in a battery draining operational mode for extended periods of time.

28 Claims, 8 Drawing Sheets

U.S. PATENT DOCUMENTS

| | | | |
|---|---|---|---|
| 2,196,667 A | | 4/1940 | Moseley |
| 2,250,975 A | | 7/1941 | Sussman |
| 2,445,635 A | * | 7/1948 | Poliakoff |
| 2,558,332 A | | 6/1951 | Artale |
| 3,242,516 A | | 3/1966 | Cantor |
| 3,400,417 A | | 9/1968 | Moret |
| 3,509,874 A | | 5/1970 | Stillman |
| 3,733,634 A | | 5/1973 | Golbe |
| 3,775,800 A | | 12/1973 | Veneziani |
| 3,802,420 A | | 4/1974 | Moffat et al. |
| 4,048,690 A | | 9/1977 | Wolfson |
| 4,156,620 A | | 5/1979 | Clemens |
| 4,203,431 A | | 5/1980 | Abura et al. |
| 4,397,055 A | | 8/1983 | Cuchiara |
| 4,420,851 A | | 12/1983 | Wiener |
| 4,476,602 A | | 10/1984 | Hurn et al. |
| 4,795,347 A | | 1/1989 | Maurer |
| 4,827,550 A | | 5/1989 | Graham et al. |
| 4,845,795 A | | 7/1989 | Crawford et al. |
| 4,897,517 A | | 1/1990 | Gundlach |
| 4,964,398 A | | 10/1990 | Jones |
| 4,989,287 A | * | 2/1991 | Scherer |
| 5,033,150 A | | 7/1991 | Gross et al. |
| 5,035,020 A | | 7/1991 | Winiewski |
| 5,054,149 A | | 10/1991 | Si-Hoe et al. |
| 5,056,265 A | | 10/1991 | Hurst |
| D321,285 S | | 11/1991 | Hirabayashi |
| 5,070,567 A | | 12/1991 | Holland |
| 5,120,225 A | | 6/1992 | Amit |
| 5,142,723 A | | 9/1992 | Lustig et al. |
| D329,946 S | | 10/1992 | Curtis et al. |
| D330,286 S | | 10/1992 | Curtis et al. |
| 5,170,525 A | | 12/1992 | Cafaro |
| 5,186,627 A | | 2/1993 | Amit et al. |
| 5,226,206 A | | 7/1993 | Davidovitz et al. |
| 5,235,716 A | | 8/1993 | Stella |
| 5,253,382 A | | 10/1993 | Beny |
| 5,274,870 A | | 1/1994 | Stollman |
| 5,311,633 A | | 5/1994 | Herzog et al. |
| 5,341,534 A | | 8/1994 | Serbinski et al. |
| 5,353,460 A | | 10/1994 | Bauman |
| D352,829 S | | 11/1994 | Perry |
| 5,359,747 A | | 11/1994 | Amakasu |
| 5,378,153 A | | 1/1995 | Giuliani et al. |
| 5,396,678 A | | 3/1995 | Bredall et al. |
| 5,404,608 A | | 4/1995 | Hommann |
| D358,486 S | | 5/1995 | Loew |
| 5,416,942 A | | 5/1995 | Baldacci et al. |
| 5,435,034 A | | 7/1995 | Bigler et al. |
| 5,461,744 A | | 10/1995 | Merbach |
| D364,740 S | | 12/1995 | Loew |
| 5,494,252 A | | 2/1996 | Amit et al. |
| 5,500,970 A | | 3/1996 | Maurer et al. |
| 5,504,959 A | | 4/1996 | Yukawa et al. |
| D370,347 S | | 6/1996 | Heinzelman et al. |
| 5,524,312 A | | 6/1996 | Tan et al. |
| 5,590,434 A | | 1/1997 | Imai |
| 5,617,601 A | | 4/1997 | McDougall |
| 5,617,603 A | | 4/1997 | Mei |
| 5,625,916 A | | 5/1997 | McDougall |
| D391,083 S | | 2/1998 | Nicoll |
| 5,726,932 A | | 3/1998 | Lee et al. |
| 5,732,433 A | | 3/1998 | Göcking et al. |
| 5,784,743 A | | 7/1998 | Shek |
| D397,251 S | | 8/1998 | Eguchi et al. |
| D397,252 S | | 8/1998 | Allende |
| 5,822,821 A | | 10/1998 | Sham |
| D400,713 S | | 11/1998 | Solanki |
| 5,836,030 A | | 11/1998 | Hazeu |
| 5,839,148 A | | 11/1998 | Volpenhein |
| 5,842,244 A | | 12/1998 | Hilfinger et al. |
| 5,842,249 A | | 12/1998 | Sato |
| 5,850,655 A | | 12/1998 | Göcking et al. |
| D403,510 S | | 1/1999 | Menke et al. |
| 5,867,856 A | | 2/1999 | Herzog |
| D406,464 S | | 3/1999 | Yost et al. |
| 5,876,206 A | | 3/1999 | Maurer |
| 5,901,397 A | | 5/1999 | Häfele et al. |
| D414,607 S | | 10/1999 | Trojnowski et al. |
| 5,996,157 A | | 12/1999 | Smith et al. |
| 6,000,083 A | | 12/1999 | Blaustein et al. |
| 6,032,313 A | | 3/2000 | Tsang |
| D422,143 S | | 4/2000 | Beals et al. |
| D422,144 S | | 4/2000 | Harada |
| D428,261 S | | 4/2000 | Lee |
| D430,730 S | | 9/2000 | Klein |
| D432,312 S | | 10/2000 | Blaustein et al. |
| D433,814 S | | 11/2000 | Blaustein et al. |
| D434,563 S | | 12/2000 | Lim et al. |
| D434,565 S | | 12/2000 | Bojar |
| 6,178,579 B1 | | 1/2001 | Blaustein et al. |
| 6,178,582 B1 | | 1/2001 | Halm |
| D437,688 S | | 2/2001 | Beals et al. |
| 6,189,693 B1 | | 2/2001 | Blaustein et al. |
| D440,048 S | | 4/2001 | Beals et al. |
| D444,629 S | | 7/2001 | Etter et al. |
| D446,941 S | | 8/2001 | Kraemer |
| D448,171 S | | 12/2001 | Harris et al. |

FOREIGN PATENT DOCUMENTS

| | | |
|---|---|---|
| CN | 2324987 | 6/1999 |
| CN | 2393503 | 8/2000 |
| DE | 27 36 286 A1 | 12/1978 |
| DE | 3406-112 A | 8/1985 |
| DE | 41 39 788 A1 | 6/1993 |
| DE | 296 00 236 U1 | 1/1996 |
| DE | 296 00 255 U1 | 1/1996 |
| DE | 296 13 608 U1 | 8/1996 |
| DE | 296 18 755 | 10/1996 |
| DE | 297 01 302 U | 1/1997 |
| DE | 298 21 121 U1 | 11/1998 |
| EP | 0 254 397 | 1/1988 |
| EP | 0 520 985 B1 | 5/1990 |
| EP | 0 537 465 A2 | 4/1993 |
| EP | 0 569606 A1 | 11/1993 |
| EP | 0 990 424 A1 | 4/2000 |
| EP | 1 053 721 | 5/2000 |
| FR | 2434681 | 8/1978 |
| GB | 121116 | 6/1919 |
| GB | 184975 | 8/1922 |
| GB | 2 228 861 A | 9/1990 |
| GB | 2 290 224 | 5/1994 |
| JP | 5-95816 * | 4/1993 |
| JP | 15-146314 | 6/1993 |
| JP | 5-199917 | 8/1993 |
| JP | 6-245820 | 9/1994 |
| KR | 81-001648 | 4/1981 |
| KR | 81-001646 | 10/1981 |
| KR | U1986-0001137 | 6/1986 |
| SE | 324 221 | 5/1970 |
| TW | 137856 | 7/1990 |
| TW | 239963 | 2/1995 |
| TW | 239 964 | 2/1995 |
| TW | 253174 | 8/1995 |
| TW | 330411 | 4/1998 |
| WO | WO 93/20777 | 10/1993 |
| WO | WO 94/09676 | 10/1993 |
| WO | WO 95/31123 | 11/1995 |
| WO | WO 98/26730 | 6/1998 |
| WO | WO 98/46103 | 10/1998 |
| WO | WO 99/12492 | 3/1999 |

| | | |
|---|---|---|
| WO | WO 99/65359 | 12/1999 |

OTHER PUBLICATIONS

Bader, Herbert I., "Review of Currently Available Battery–Operated Toothbrushes", Compendium Continuing Education in Dentistry, vol. XIII, No. 12, Dec. 1992, pp. 1162–1167.

Photos of Bio Brush Industries (See IDS filed May 31, 2002 in U.S. Ser. No. 09/991,772, filed Nov. 16, 2001, withdrawn, and refiled as Continuation application U.S. Ser. No. 10/082,503, filed Feb. 25, 2002, Exhibits A,B,C).

* cited by examiner

ELECTRIC TOOTHBRUSH

This application is a continuation-in-part of application Ser. No. 09/710,616, filed on Nov. 9, 2000, which issued as U.S. Pat. No. 6,371,294 on Apr. 16, 2002, which is a continuation-in-part of application Ser. No. 09/382,745, filed on Aug. 25, 1999, which issued as U.S. Pat. No. 6,178,579 on Jan. 30, 2001, and which is a continuation-in-part of application Ser. No. 09/236,794, filed Jan. 25, 1999, which issued as U.S. Pat. No. 6,189,693 on Feb. 20, 2001, and which is a continuation-in-part of application Ser. No. 09/163,621, filed on Sep. 30, 1998, which issued as U.S. Pat. No. 6,000,083 on Dec. 14, 1999.

BACKGROUND OF THE INVENTION

The present invention relates generally to electric toothbrushes. More particularly, it relates to an improved battery powered toothbrush.

The benefits of brushing one's teeth using motorized toothbrushes are well known, and motorized movement in toothbrushes has been the subject of much recent innovation and design activity. Also, the commercial market has seen the introduction, over the last several years, of many different types of motorized toothbrushes. However, an examination of the available technology shows a tendency toward increasingly complex, expensive, and non-commercially feasible methods of achieving motorized motions in the bristles and heads of toothbrushes to aid in more effectively cleaning one's teeth.

The commercial marketplace has become divided into two price markets. On the higher priced end are some of these more complex motorized toothbrushes that provide various motions to the bristles and brush head. The lower end of the market has become the province of very simple motorized toothbrushes that only vibrate through the use of an offset weight attached to the motor shaft, and which provide very little true additional cleaning benefit with their use, since no vigorous motion is transmitted to the cleaning surface of the brush. The vibrations are also very uncomfortable to the hand and act as a disincentive to brush one's teeth for an adequate time.

Numerous electric toothbrushes have been developed over the years. Some known devices are shown in U.S. Pat. Nos. 5,070,567; 5,186,627; 5,274,870; 5,341,534; 5,378,153; and 5,732,433. None of these toothbrushes provides a low cost/hygienic means for a customer to try the toothbrush before making a toothbrush purchase. Allowing a customer to observe the operation of a motorized toothbrush, feel the level of vibration, and hear the sound of the toothbrush is a powerful mechanism for communicating the usefulness and convenience of the toothbrush. Accordingly it has been considered desirable to develop an electric toothbrush which overcomes difficulties of prior art toothbrushes and provides a means for a customer to try the toothbrush without removing the toothbrush from its package and even before purchasing the toothbrush.

SUMMARY OF THE INVENTION

To those ends a new electric toothbrush has been developed. The new electric toothbrush comprises packaging for containing the toothbrush, and a body portion having a first end and a hollow portion. A head located at the first end includes a moving portion, the moving portion comprises at least one of bristles and massaging tips. A motor located within the hollow portion of the body portion is operative to generate motion for driving the moving portion. A first switch is operably connected to the motor. The first switch can be actuated in a first manner to provide momentary operation of the toothbrush even when the toothbrush is inside the packaging.

In some embodiments the first switch is depressed to provide the momentary operation. For example, in some embodiments, the first switch is a push button.

In some embodiments, the toothbrush further comprises a second switch, which is actuated in a second manner, to provide continuous operation of the toothbrush when the toothbrush is removed from the packaging. For example, in some embodiments, the second switch is a slide switch, a toggle switch, an alternate acting pushbutton switch, a rotary switch, electronic switch or any other switch that provides a continuous or non-momentary contact closure.

One advantage of the present invention is the provision of an electric toothbrush with a switch which allows momentary operation of the toothbrush while the toothbrush is inside sealed factory packaging.

Another advantage of the present invention is the provision of an electric toothbrush which is inexpensive and easy to manufacture.

Still another advantage of the present invention is the provision of an electric toothbrush with moving portion that rotates, swivels, oscillates or reciprocates.

Yet another advantage of the present invention is the provision of a circular portion that rotates, reciprocates, swivels, or oscillates which is positioned at the end of the brush head to facilitate easier access to the back of the user's mouth.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENTS

Figure 1:
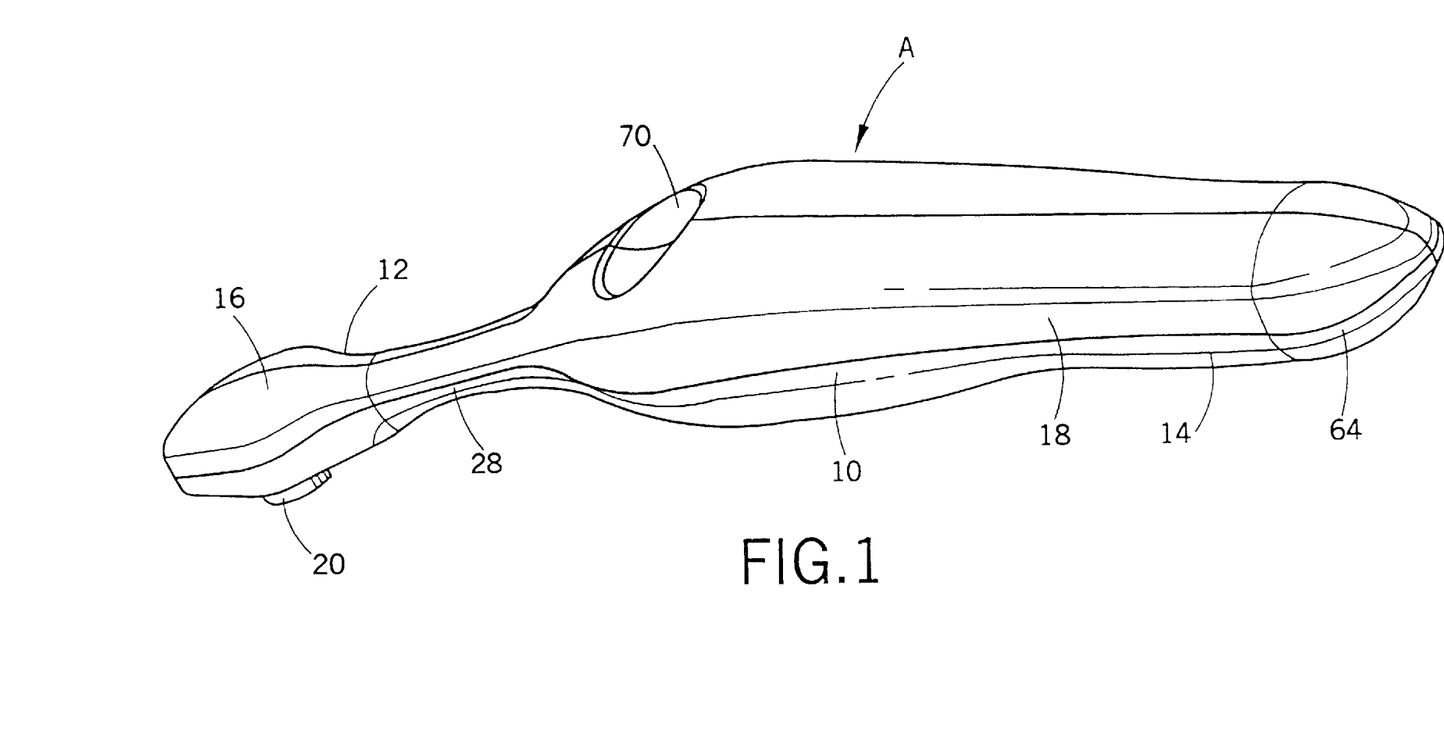
FIG. 1 is a top perspective view of a first electric toothbrush, the first electric toothbrush including a switch providing a combination of momentary and non-momentary switching features.

Referring now to the drawings wherein the showings are for the purposes of illustrating the preferred embodiments of the invention only and not for purposes of limiting same, FIG. 1 shows an first electric toothbrush A. The electric toothbrush can be used for personal hygiene such as brushing one's teeth and gums.

As shown in FIG. 1, the electric toothbrush includes an body portion 10, which has a first end 12 and a second end 14. A head 16 is located at the first end 12 and a handle 18 is located at the second end 14.

Figure 2:
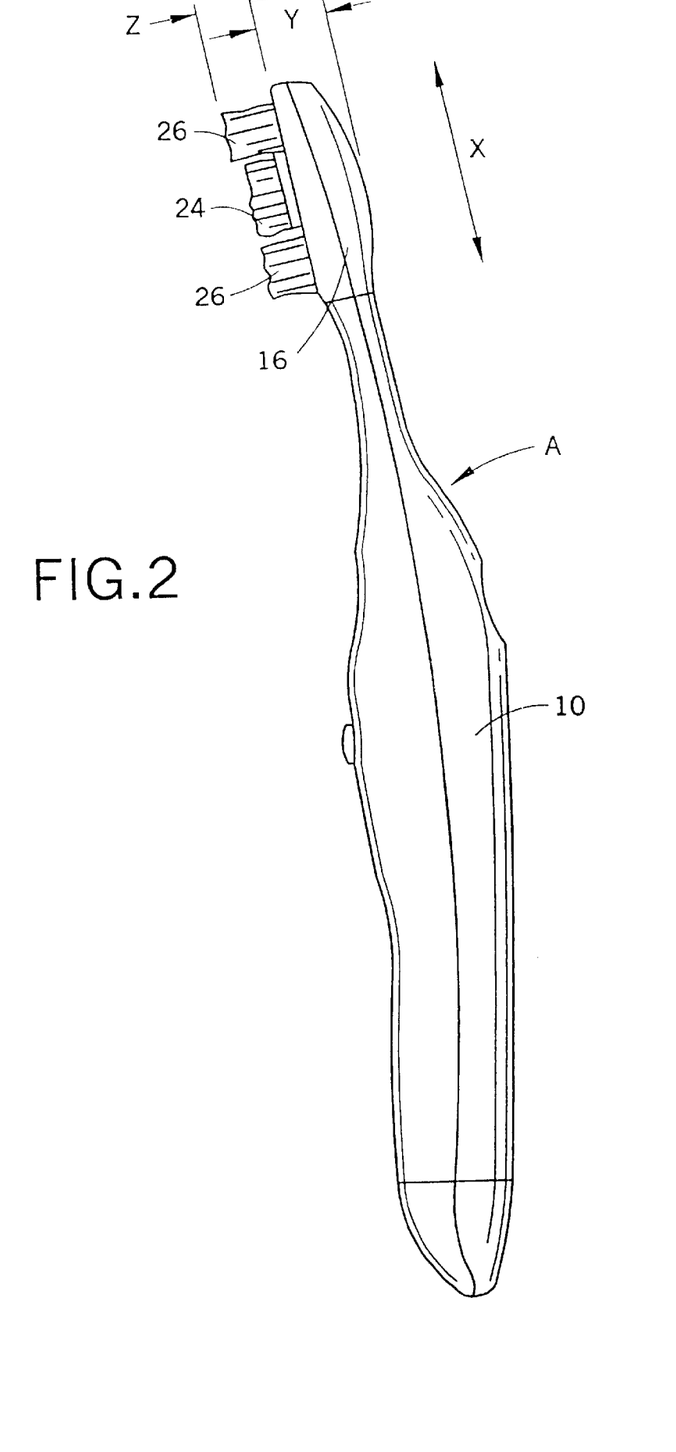
FIG. 2 is a side elevation of the first toothbrush showing details of one toothbrush head embodiment.

The exemplary head 16 has a more traditional larger brush head shape which permits the user to brush his teeth in the typical manner of an up and down fashion. As shown on FIG. 2, the length of the head 16, dimension "X", can range from about 0.75 inches to about 1.75 inches. The thickness of the brush head, dimension "Y", can range from about 0.25 inches to about 0.50 inches. The design of the head 16 allows for inexpensive manufacture and assists in bringing effective motorized rotational toothbrushes within the financial reach of a large portion of the population. However, other head designs can be used and still remain within the scope of aspects of the invention.

Figure 3:
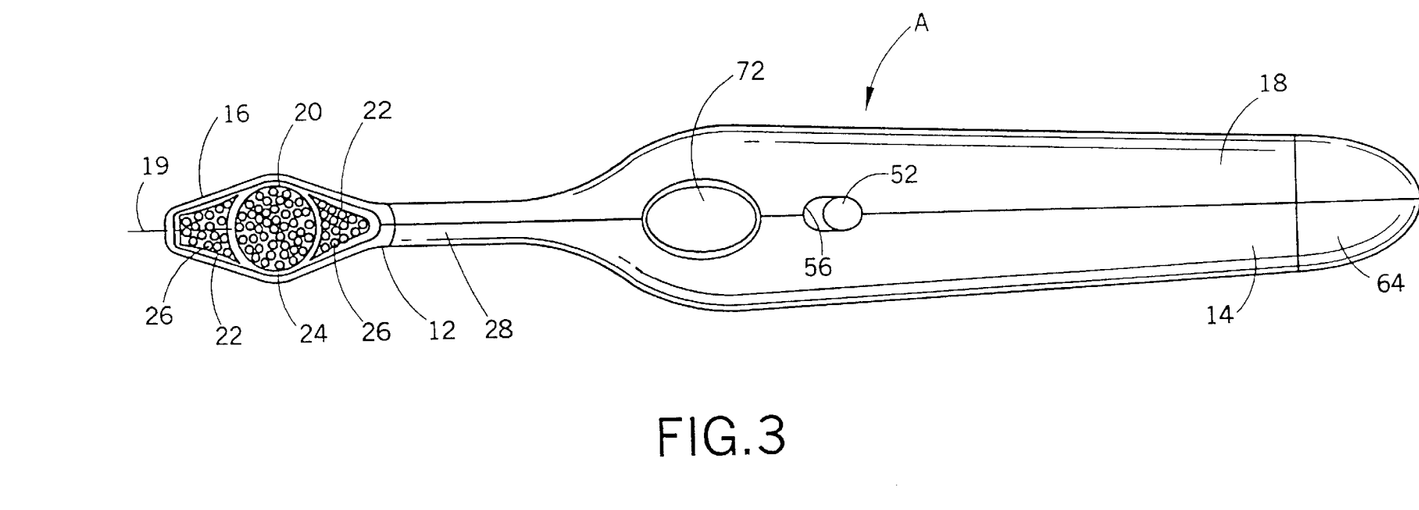
FIG. 3 is a bottom elevational view of the first electric toothbrush.

Referring now to FIG. 3, the exemplary head 16 further includes a longitudinal axis 19, an exemplary moving portion or brush head 20 and an optional static portion or brush head 22. The static portion 22 is located on opposite sides of the moving portion 20. The exemplary moving portion 20 is located at the center of the brush head 16. The exemplary moving portion 20 rotates, swivels, oscillates or reciprocates about an axis approximately normal to the longitudinal axis 19 of the brush head 16. However, other head motions are known in the art. The exemplary moving portion 20 may rotate continuously in a clockwise or counter clockwise direction or partially rotate, oscillate, or reciprocate in a back and forth manner. Alternatively, the exemplary moving portion 20 moves in some other manner. For example, U.S. Pat. No. 5,226,206 to Davidovitz et al. discloses a toothbrush with combined longitudinal reciprocation and circular rotation or oscillation. U.S. Pat. No. 5,524,312 to Tan et al. discloses a toothbrush with a first moving portion moving in a wiping motion described as oscillation in a transverse direction and a second moving portion that moves round about its own center. U.S. Pat. No. 5,070,567 to Holland discloses a toothbrush with a combined rotational and revolving motions. U.S. Pat. No. 5,253,382 to Beny discloses a toothbrush with combined longitudinal and transverse motions resulting in a figure eight type brush movement. In addition to the motions disclosed herein, any known moving portion motion may be incorporated and still remain within the scope of aspects of the invention.

The exemplary moving portion 20 includes stiff bristles 24. The optional static portion 22 includes soft bristles 26. The stiff bristles 24 are slightly recessed with respect to the soft bristles 26. The stiff bristles 24 aid in the deep cleaning and plaque removal process, while the stationary soft bristles 26 are softer so as to not damage the gums. The thickness of the bristles, dimension "Z", shown in FIG. 2, can range from about 0.25 inches to about 0.75 inches. Again, other bristle arrangements may be used and still remain within the scope of aspects of the invention.

Referring again to FIG. 3, the body portion 10 further includes an angled shaft 28, located between the head 16 and the handle 18. The angled shaft 28 provides an ergonomic benefit that has not been utilized on a motorized toothbrush. The angle is well known for its ergonomic benefit in permitting easier access into the back recesses of the mouth while still contacting the tooth surface.

Figure 4:
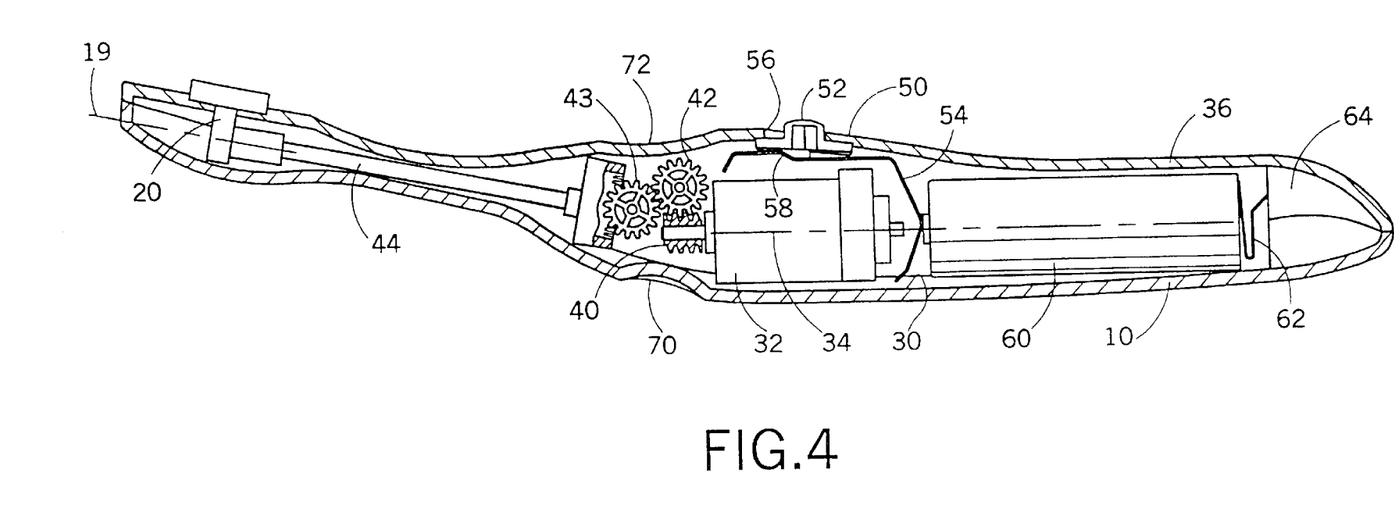
FIG. 4 is a side elevational view in cross section of the one embodiment of the first electric toothbrush.

As shown in FIG. 4 the elongated body portion 10 further includes a hollow portion 30 which houses a motor 32. The motor 32 has a longitudinal axis 34 in line with a longitudinal axis 36 of the elongated body portion 10. However, other motor arrangements may be used and still remain within the scope of aspects of the invention.

The motor 32 generates motion for driving the moving portion 20. Optionally, the moving portion 20 is driven through a driving means. For example, motion generated by the motor 32 is delivered to the moving portion 20 to move, rotate, oscillate or reciprocate through a driving means including a worm gear 40 and a pair of step gears 42, 43. The motor 32 is operatively connected to the worm gear 40. Step gear 42 is operatively connected to step gear 43 and the worm gear 40.

As shown in FIG. 4, the first step gear 42 permits the matching second step gear 43 to be offset with respect to the longitudinal axis 36 of the elongated body portion 10.

As shown in FIG. 4, the exemplary driving means further includes a shaft 44 that is connected at a first end to the offset step gear 43 and at a second end to the moving portion 20. The second step gear 43 is placed at a desired angle so that the shaft 44 itself can still be straight, thus losing no power or torque through the added function of a flexible shaft.

However, other driving means can be used. For example, U.S. Pat. No. 4,827,550 Graham et al. discloses a toothbrush having a reciprocating rack for driving a plurality of geared brush heads in a rotational oscillatory manner. U.S. Pat. No. 3,242,516 to H. Cantor discloses a toothbrush having conical drive gears, pulleys and a belt for rotating a moving portion. U.S. Pat. No. 5,617,601 to McDougall discloses a toothbrush having a reciprocating flexible member for driving a moving portion in a rotational or oscillatory manner. U.S. Pat. No. 5,226,206 to Davidovitz et al. discloses a toothbrush with a reciprocating shaft and a carrier member. The carrier member carries a geared brush head. The geared brush head is in meshed engagement with a stationary rack element. As the shafted reciprocates, the brush head reciprocates. Additionally, due to the meshed engagement with the rack element, the brush head also rotates. In addition to the driving means disclosed herein, any known driving means can be used and stay within the scope of aspects of the invention.

A switch 50 is provided to control operation of the electric toothbrush and is operatively connected to the motor 32. For example, the switch 50 includes a molded actuator button 52 and a metal contact 54 disposed within aperture 56. In a momentary mode of operation, the switch 50 is manually depressed by pressing a molded actuator button 52 down, which then presses against a metal contact 54, which completes the circuit and provides momentary operation of the toothbrush. The switch 50 also allows continuous mode of operation through a ramp design. Sliding the button 52 forward toward the head 16 provides for continuous operation. A selected shape of the button combined with a molded or stamped in ramp 58 in the metal contact 54, causes forward movement of the button 52 to move the contact 54 downward, thereby completing the circuit. The toothbrush then continuously operates until the button 52 is slid back into an off position toward the handle 18 and the button 52 disengages the metal contact 54.

Figure 7:
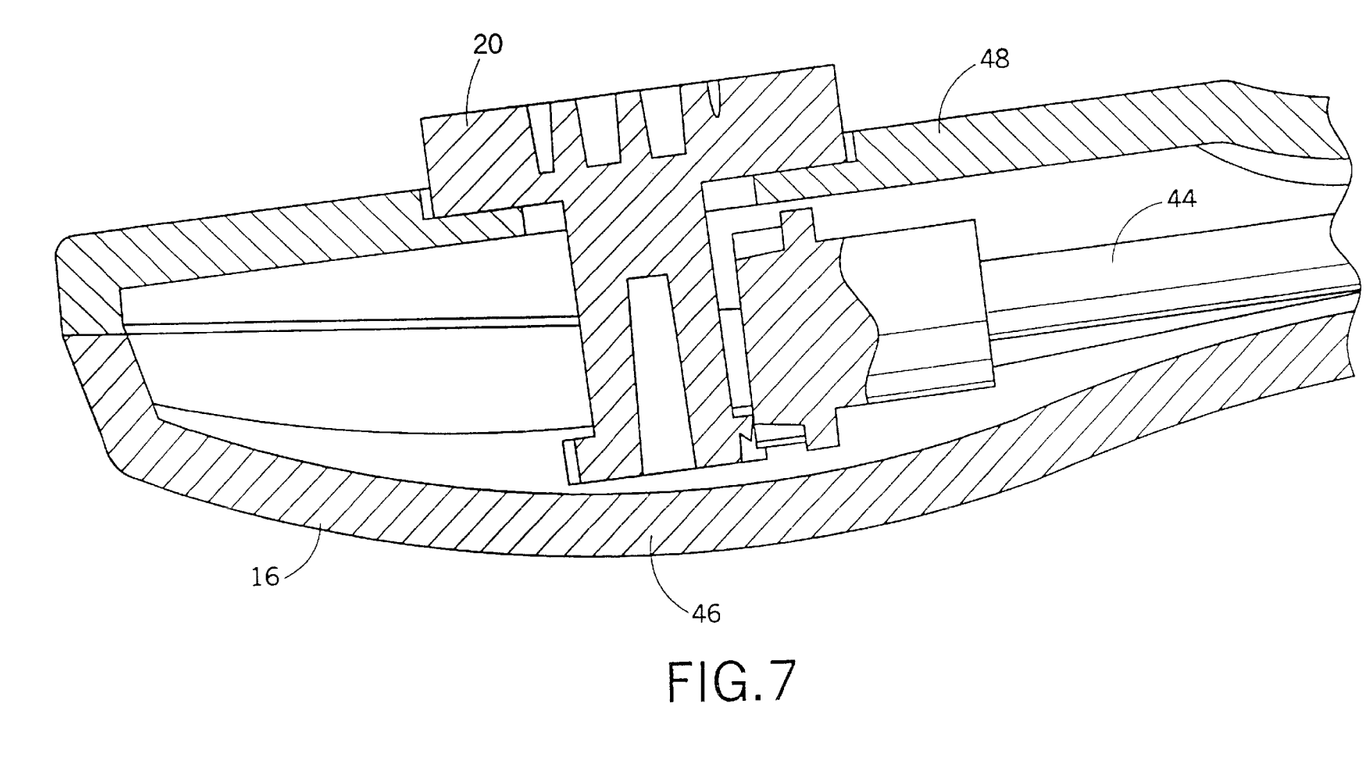
FIG. 7 is a front and side elevational view of an electric toothbrush in packaging.

By providing the momentary function, the toothbrush can be packaged in packaging as shown in FIG. 7 where the consumer can depress the button 52 through the packaging and see, feel and hear its operation while the toothbrush is still inside the packaging. When the toothbrush is purchased and removed from the package the consumer is able to us the non-momentary, continuous mode, or ramp design function to operate the toothbrush in a continuous manner. FIG. 7 illustrates one version of the button 52. By testing the operation of the toothbrush in this manner, the consumer can easily evaluate the quality of the toothbrush. For example, the consumer can evaluate the quietness of the operation of the toothbrush. The consumer can determine that the vibration of the toothbrush is not uncomfortable. The consumer can sense the strength or torque behind the brushing action and the consumer can verify that batteries installed in the toothbrush are fully charged. It should be noted, as detailed below, that other sizes and shapes of buttons as well as functional configurations may be used.

Referring again to FIG. 4, a battery 60 is provided within the hollow portion 30 of the elongated body portion 10. A battery terminal or contact 62 is provided for the battery 60. An AA size battery can be used as is illustrated in FIG. 4. To install the battery 60 into the hollow portion 30, a slidable snap-on cover 64 is depressed and slid off the end of the handle 18 to expose the hollow portion 30. The battery 60 is inserted, then the cover 64 is slid back on to the housing and snapped into place. The terminal end of the battery 60 is then in contact with the metal contact 54.

If desired, depressions or grip areas 70 and 72 can be molded into the body 10 as shown in FIG. 4. The depressions 70, 72 are used to support a user's thumb and forefinger or other fingers to make using the electric toothbrush easier and more comfortable.

Alternatively, the switch 50 may be only a momentary switch that does not provide a continuous mode of operation. In that case, the consumer is still able to evaluate the quality of the toothbrush before purchasing it. However, in operation the consumer is required to hold the switch 50 in the closed position while using the toothbrush.

In other embodiments, momentary and continuous switching functions are provided by two separate switches. For example, referring to FIG. 5, a second electric toothbrush B includes a body portion 80 which has a first end 82 and a second end 84. A head 86 is attached to or located at the first end 82 and a handle 88 is attached to or located at the second end 84. A first switch 90 and a second switch 92 are mounted in the body portion 80. The exemplary head 86 includes a moving portion 94 and a static portion 96. The moving portion and the static portion contain brushing elements such as bristles 98 and or massaging tips 100.

Figure 5:
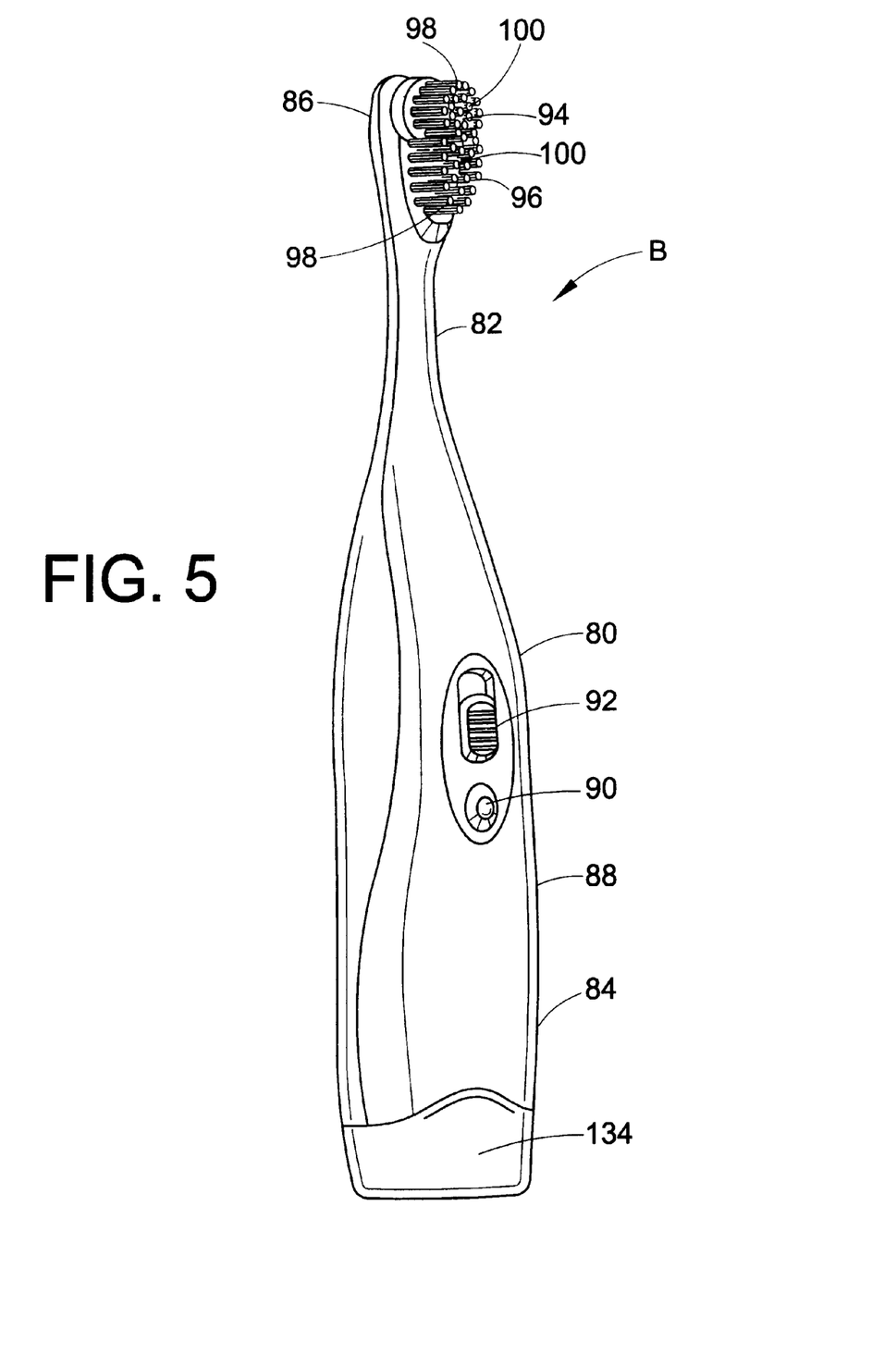
FIG. 5 is a perspective view of a second electric toothbrush, the second electric toothbrush including a switching circuit including a first switch or switching member operative to providing a momentary switching function and a second switch or switching member operative to provide a non-momentary switching feature.

The first switch 90 is a momentary switch. For example, the first switch 90 is a push button that operates in a manner similar to the switch 50 when the switch 50 is operated in the momentary mode.

Alternatively, the first switch may be another kind of momentary switch as long as the first switch can be easily actuated while the second toothbrush B is sealed in factory packaging, such as, that depicted in FIG. 7.

The second switch 92 is a non-momentary or continuous mode switch. For example., the second switch 92 is a slide switch that operates in a manner similar to the switch 50 when the switch 50 is operated in the continuous mode.

Figure 8:
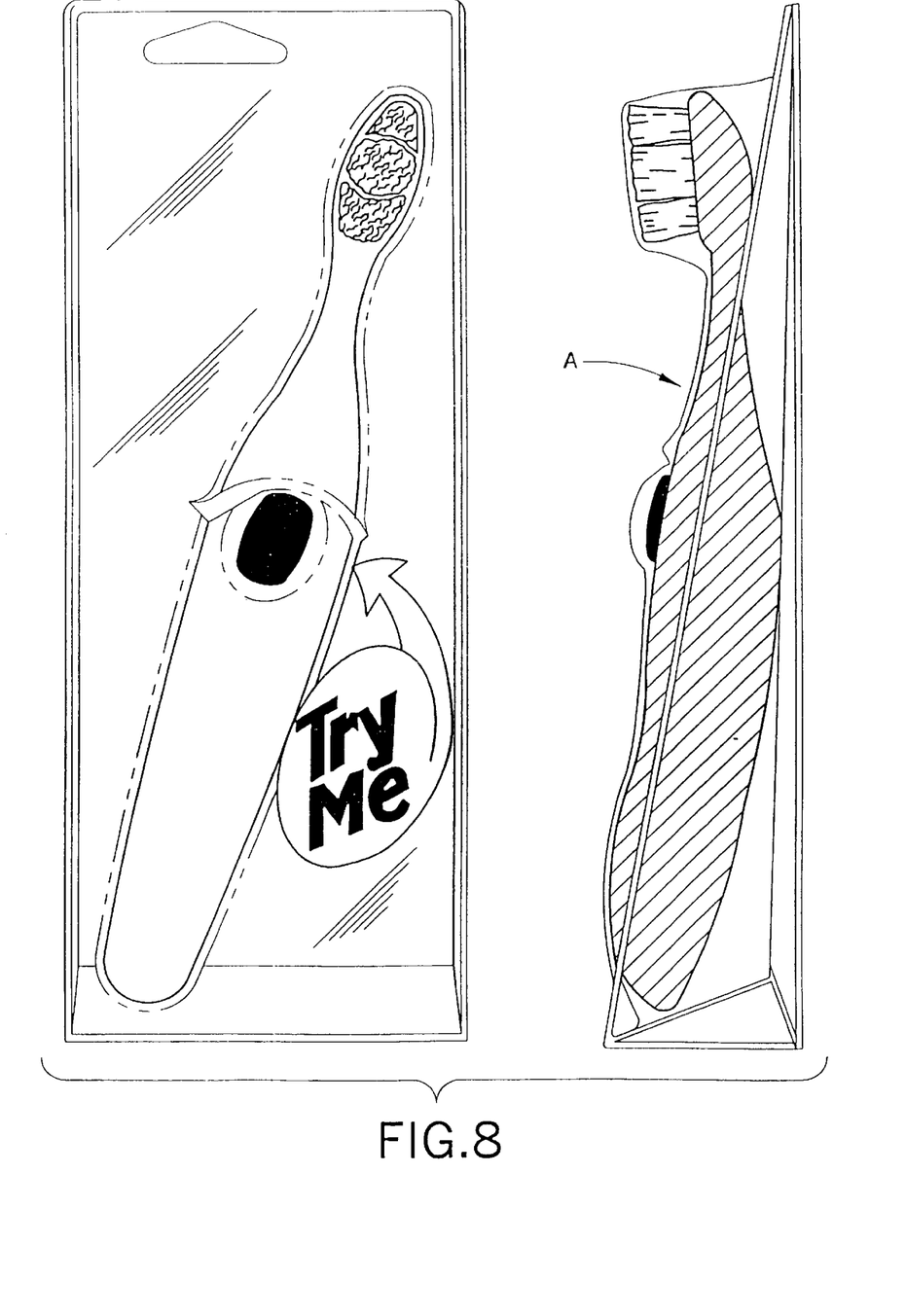
FIG. 8 is a perspective view of a fourth toothbrush showing details of an exemplary motor, driving means and moving portion.

Alternatively, the second switch 92 may be any other kind of non-momentary switch, as long as the second switch can not be easily actuated while the toothbrush B is sealed in factory packaging, such as that depicted in FIG.8. In this regard, the factory packaging may be designed to prevent or impede attempts to actuate the second switch.

Figure 6:
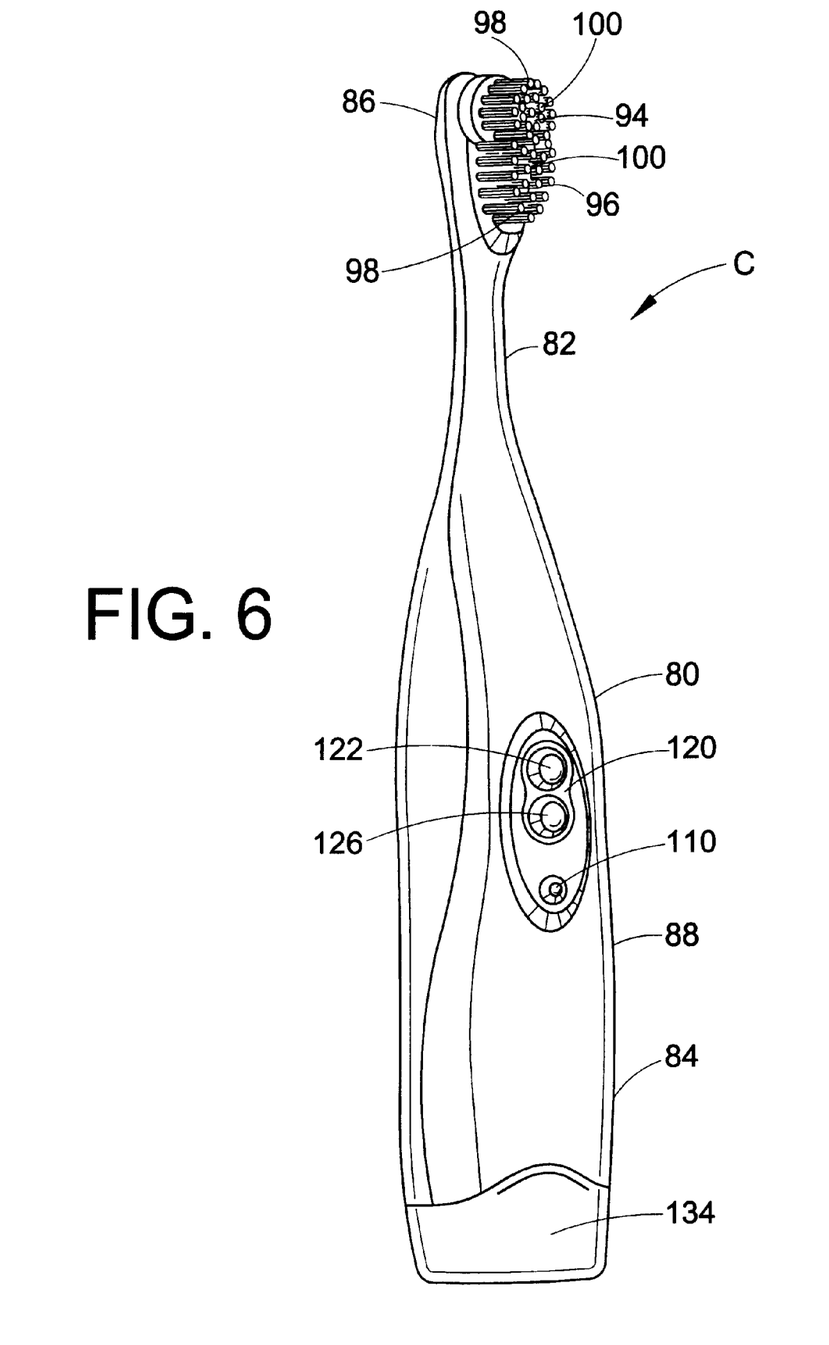
FIG. 6 is a perspective view of a third electric toothbrush, the third electric toothbrush including a switching circuit including a third switch or switching member operative to providing a momentary switching function and a fourth switch or switching member operative to provide a non-momentary switching feature.

Referring to FIG. 6, a third toothbrush C also includes a body portion 80 which has a first end 82 and a second end 84. A head 86 is located at the first end 82 and a handle 88 is attached to the second end 84. A third switch 110 and a fourth switch 120 are mounted in the elongated body portion 80. The head includes a moving portion 94 and a static portion 96. The moving portion and the static portion contain brushing elements such as, bristles 98 and/or massaging tips 100.

The third switch 110 is a momentary switch. The third switch may be similar to the second switch 90. Alternatively, the third switch may be any other kind of momentary switch. For example, the third switch 110 may be part of an electronic switching circuit comprising a micro-controller circuit (hidden from view) having a first input and an output. The first input senses the state of the third switch button 110. The micro-controller controls the state of the output based on sensed input. For example, the micro-controller closes an electronic switch, such as, for example, a FET type transistor, for a predetermined period of time, for example, 4 seconds, whenever the third switch button 110 is momentarily depressed. Alternatively, the microprocessor closes an electronic switch whenever, and for as long as, the third switch button 110 is depressed.

The fourth switch 120 is a non-momentary push button switch. For example, the fourth switch includes a first switching member 122 and a second switching member 126. Depressing the first switching member 122 closes a contact thereby powering the toothbrush. Depressing the second switching member 126 opens the contact, thereby de-powering the toothbrush. If necessary, a toothbrush package may be designed to make it difficult to accidentally or maliciously activate the fourth switch 120 while the toothbrush is in the package. For example, a blister package may include a dome over the fourth switch 120 that can not be easily depressed. Alternatively, the blister package is dimensioned so there is generally a large gap between the toothbrush switches and the blister. A recess may be provided in the blister that reaches toward the third switch 110 thereby permitting momentary trials of the toothbrush.

Alternatively, the fourth switch 120 is another kind of non-momentary or continuous mode switch. Such switches are known. For example, a non-momentary toggle switch, a push on/push off switch, an alternate acting push button switch or a rotary switch can be used. Alternatively the second switch is part of an electronic switching circuit. For example the micro-controller mentioned above also includes a second input. The second input senses the state of the first switching member 122. When the micro-controller senses that the first switching member is momentarily depressed, the micro-controller closes the electronic switch until an off command input is sensed. For example, the electronic switch is closed until the first switching member 122 is momentarily depressed a second time. Alternatively, a third input is monitored in order to sense the state of the second switching member 126 and the micro-controller opens the electronic switch when the second switching member is momentarily depressed.

The switching member combinations and micro-controller responses described here are exemplary only. Any set of inputs and responses can be included. For example, a predetermined pattern of switching member actuations or depressions may cause the micro-controller to repeatedly open and close the electronic switch thereby causing the moving portion to move in a pulsed manner. Alternatively, in a battery saving mode the micro-controller may open the electronic switch after a prolonged period of operation even if no off command input is sensed.

A fourth electric toothbrush D is shown in FIG. 8. The electric toothbrush D includes an body portion 150 which has a first end 152 and a second end 154. A head 160 is attached to the first end 152 and a handle 162 is attached to the second end 154.

The head 160 further includes an moving portion or brush head 164, a static portion or brush head 166, a first end 168, and a second end 170. As shown in FIG. 8, the moving portion 164 is located adjacent the second end 170. The static portion 166 is shown located adjacent the first end 168. However, it is to be appreciated that the moving portion 164 could be located adjacent the first end 168, and the static portion 166 could be located adjacent the second end 170. Furthermore, the moving portion 164 could be positioned in the center of the brush head with static portions 166 on opposite sides of the moving portion 164 similar to that shown in FIG. 3.

In accordance with this embodiment, the moving portion 164 oscillates about an axis approximately normal to a longitudinal axis 172 of the elongated body portion 150.

The moving portion 164 can include stiff bristles 178. The static portion 166 can include soft bristles 180 which are softer than the stiff bristles. The stiff bristles 178 may be slightly recessed with respect to the soft bristles 180. The stiff bristles 178 aid in the deep cleaning and plaque removal process, while the stationary soft bristles 180 are softer so as to not damage the gums.

The body portion 150 further includes an angled shaft 190, an upper housing 192 (not shown), and a lower housing 194. The angled shaft 190 is located between the head 160 and the handle 162. The angled shaft 190 provides an ergonomic benefit that has not been utilized on a motorized toothbrush.

The body portion 150 of the fourth toothbrush also includes a hollow portion 196 which houses a motor 200. The hollow portion 196 is formed between the upper housing 192 and the lower housing 194. The motor 200 generates motion for driving the moving portion 164 to rotate, oscillate, or reciprocate. Again, in addition to the motion disclosed herein, any known motion can be provided and still remain within aspects of the present invention. Power is provided to the motor by battery as shown and described for the first, second and third toothbrushes A, B, C.

It should be understood that the forth electric toothbrush D includes any of the switching arrangements discussed above in reference to the first, second and third toothbrushes A, B, C. For clarity, views and discussion of the switches are not repeated here.

The fourth toothbrush D further includes a first gear 202 which is operatively connected to and powered by the motor 200. The first gear 202 rotates about the longitudinal axis 172 of the elongated body portion 150. A second gear 206 is operatively connected to the first gear 202. The second gear 206 is approximately normal to the first gear 202. The second gear 206 rotates about an axis approximately normal to the longitudinal axis 172. Teeth 208 of the first gear 202 mesh with teeth 210 of the second gear 206, thus causing second gear 206 to rotate when first gear 202 rotates.

A first swivel arm 220 is pivotably connected to the second gear 206 via a pin 222 or other fastening device. A second swivel arm 224 is pivotably connected to the first swivel arm 220 via a pin 226 or other fastening device. A shaft 230 is fixedly secured at a shaft first end 232 to the second swivel arm 224. The shaft 230 is pivotably attached at a shaft second end 234 to a third swivel arm 240. The shaft 230 is housed within the angled shaft 190.

The shaft 230 is generally parallel with the longitudinal axis 172.

A guide spacer 250 is located within the angled shaft 190 and surrounds the shaft 230 adjacent the first end 232 of the shaft 230 to minimize lateral movement of the shaft 230. A second guide spacer 252 is located adjacent the second end 234 of the shaft 230 to also minimize lateral movement of the shaft 230. Guide spacers 250, 252 align the shaft 230 within the angled shaft 190 and minimize its movement from side to side within the angled shaft 190.

The third swivel arm 240 has a first end 244 and a second end 246. The third swivel arm 240 is pivotably connected to the second guide spacer 252 at the swivel arm first end 244 via a pin 253. The third swivel arm 240 is connected at the swivel arm second end 246 to the moving portion 164 via a pin 254 or other fastening device. The pin 254 is connected to a disk 256 of the moving portion 164 which is housed within the head 160.

As the first gear 202 rotates, the second gear 206 is rotated, thus moving the first swivel arm 220 in a back and forth circular fashion about the second gear 206 and along the longitudinal axis 172. The first swivel arm 220 also can pivot about the pin 222. The first swivel arm 220 retains its orientation of approximately parallel to the longitudinal axis 172 of the elongated body portion 150 during movement. The second swivel arm 224 pivots with respect to its pin connection 226 with the first swivel arm 220 thus allowing the shaft 230 to oscillate in a back and forth manner toward and away from the brush head with minimal lateral motion.

During operation, the third swivel arm 240 moves back and forth along the longitudinal axis 172 of the elongated body portion 150 along with the shaft 230.

The swivel arm 240 can also pivot or move slightly laterally in a direction perpendicular to the longitudinal axis.

The third swivel arm 240 has an offset arm 260 which is offset from the longitudinal axis 172 and moves the disk 256 of the moving portion 164 in a partially rotating or oscillating motion. As the third swivel arm 240 moves back and forth, the offset arm 260 moves along an outside edge 262 of the disk 256 in a partially rotating or oscillating fashion about an axis which is approximately normal to the longitudinal axis 172. This causes the bristles 178 to also move in a partially rotating or oscillating manner about an axis approximately normal to the longitudinal axis 172.

When the third swivel arm 240 rotates, the disk 256 also rotates about an axis approximately normal to the elongated body portion longitudinal axis 172. The third, swivel arm 240 also retains its orientation of approximately parallel to the elongated body portion longitudinal axis 172 during movement.

If desired, raised grip areas (not shown) can be provided which are similar to raised grip areas 138 and 140 shown in FIG. 9 and FIG. 11 for the second preferred embodiment. The raised grip areas can be molded into the lower housing 194.

The electric toothbrushes A, B, C, D can be packaged in packaging as shown in FIG. 7. As shown for the first toothbrush A, the consumer can depress the button 90 through the packaging and see its operation while the toothbrush is inside the packaging.

As shown in FIGS. 4, 5 and 6 the toothbrushes A, B, C, D also have a battery 60 with a battery terminal or contact 62 provided within the hollow portion 30 of the body portion 80. To install the battery 60 into the hollow portion 30, a cover 64, 134 is slid off the end of the handle 18, 88 to expose the hollow portion 30. The battery 60 is inserted, then the cover 64, 134 is slid back on to the housing and snapped into place.

The invention has been described with reference to the preferred embodiments. Obviously, modifications and alterations will occur to others upon a reading and understanding of this specification. For example, still other switch combinations and packages can be applied. The package does not have to be a blister pack. For example, the package may comprise a cardboard box including holes, windows or other provisions for allowing a customer to actuate the momentary switch, and sense and view the operation of the toothbrush. Other head designs, including other moving portions with other patterns of motion and other driving means can be included. The components and features described in relation to each of the exemplary toothbrushes A, B, C, D can be shared and included in other combinations. The invention is intended to include all such modifications and alterations insofar as they come within the scope of the appended claims or the equivalents thereof.

Having thus described the invention, the invention is claimed:

1. An electric toothbrush comprising:
packaging for containing the toothbrush;
a body portion having a first end, and a hollow portion;
a head located at said first end, wherein said head includes a moving portion, wherein said moving portion comprises at least one of bristles and massaging tips;
a motor located within said hollow portion of said body portion, said motor operative to generate motion for driving the moving portion;
a first switch which is operably connected to said motor, wherein said switch can be actuated in a first manner to provide momentary operation of said toothbrush even when said toothbrush is within said packaging and a second switch actuated in a second manner to provide continuous operation of said toothbrush when said toothbrush is removed from said packaging.

2. The toothbrush as defined in claim 1 wherein said first switch is depressed to provide the momentary operation.

3. The toothbrush as defined in claim 1 wherein said first switch comprises an electronic switching circuit.

4. The toothbrush as defined in claim 1 wherein said second switch is actuated by sliding a switching member from a first position to a second position.

5. The toothbrush as defined in claim 1 wherein the second switch is actuated by depressing a switching member, wherein a first depression of the switching member closes a contact and a second depression of the switching member opens the contact.

6. The toothbrush as defined in claim 1 wherein the second switch is actuated by depressing one of a first switching member and a second switching member, wherein depressing the first switching member closes a contact and depressing the second switching member opens the contact.

7. The toothbrush as defined in claim 1 wherein the second switch is actuated by rotating a switching member from a first position to a second position.

8. The toothbrush as defined in claim 1 wherein said second switch comprises an electronic switching circuit.

9. An electric toothbrush operative to aid a user in cleaning teeth, the electric toothbrush comprising:
an elongated body having a handle portion, and a moving portion;
a motor disposed in the handle portion and operative to drive the moving portion;
a first switch operative to connect the motor to a power source only while the switch is held in a closed position by the user and a second switch operative to connect the motor to a power source when the second switch is placed in a closed position, the second switch further operative to remain in the closed position even after the switch is released by the user.

10. The electric toothbrush of claim 9 wherein the first switch comprises a momentary switch.

11. The electric toothbrush of claim 9 wherein the first switch comprises an electronic switching circuit.

12. The electric toothbrush of claim 9 wherein the first switch comprises a push button switch.

13. The electric toothbrush of claim 9 wherein the second switch comprises a toggle switch.

14. The electric toothbrush of claim 9 wherein the second switch comprises an electronic switching circuit.

15. The electric toothbrush of claim 9 wherein the second switch comprises a push button switch.

16. The electric toothbrush of claim 9 wherein the second switch comprises an alternate acting push button switch.

17. The electric toothbrush of claim 9 wherein the second switch comprises a rotary switch.

18. The electric toothbrush of claim 9 further comprising a driving means operative to drive the moving portion in a reciprocating manner.

19. The electric toothbrush of claim 9 further comprising a driving means operative to drive the moving portion in an oscillatory manner.

20. The electric toothbrush of claim 9 further comprising a driving means operative to drive the moving portion in a rotational manner.

21. The electric toothbrush of claim 9 further comprising a driving means operative to drive the moving portion in a figure eight pattern.

22. The electric toothbrush of claim 9 further comprising a driving means operative to drive the moving portion in a wiping motion.

23. An electric toothbrush comprising:
an elongated body portion having opposed first and second ends, a hollow portion and a longitudinal axis;
a head attached to said first end;
a moving portion within the head;
a motor located within said hollow portion of said elongated body portion;
a momentary switch and a non-momentary switch, both operative to connect the motor to a power source;
a gear located in said hollow portion, wherein said motor is operatively connected to said gear;
a plurality of swivel arms, wherein one swivel arm is pivotably connected to said gear; and
a shaft operatively connected to the one swivel arm and disposed for translating movement in a back and forth manner to the moving portion.

24. An electric toothbrush comprising:
an elongated body portion having opposed first and second ends, a hollow portion and a longitudinal axis;
a head attached to said first end;
a motor located within said hollow portion of said elongated body portion;
a momentary switch and a non-momentary switch, both operative to connect the motor to a power source;

a first gear and a second gear located in said hollow portion, wherein said motor is operatively connected to said first gear, and said first gear is connected to said second gear;

first, second and third swivel arms, wherein said first swivel arm is connected to said second gear, said second swivel arm is pivotably connected to said first swivel arm, and said third swivel arm moves in a back and forth manner generally along said longitudinal axis; and a shaft operatively connected to said second swivel arm at a shaft first end and operatively connected to said third swivel arm at a shaft second end;

wherein said head further comprises static massaging tips and a moving portion, wherein said third swivel arm is connected to said moving portion.

25. The electric toothbrush of claim 24 wherein said moving portion rotates about an axis normal to said longitudinal axis.

26. The electric toothbrush of claim 24 wherein said moving portion oscillates about an axis normal to said longitudinal axis.

27. The electric toothbrush of claim 24 wherein said first gear rotates about said longitudinal axis and said second gear rotates about an axis generally normal to said longitudinal axis.

28. The electric toothbrush of claim 24 further including a swivel arm connected between said one swivel arm and said shaft.

* * * * *